(12) United States Patent
Porat et al.

(10) Patent No.: US 6,432,050 B1
(45) Date of Patent: Aug. 13, 2002

(54) IMPLANTABLE ACOUSTIC BIO-SENSING SYSTEM AND METHOD

(75) Inventors: Yariv Porat, Haifa; Avi Penner, Tel Aviv; Eyal Doron, Kiryat Yam, all of (IL)

(73) Assignee: Remon Medical Technologies Ltd., Caesarea (IL)

( * ) Notice: Subject to any disclaimer, the term of this patent is extended or adjusted under 35 U.S.C. 154(b) by 0 days.

(21) Appl. No.: 09/303,644

(22) Filed: May 3, 1999

Related U.S. Application Data

(63) Continuation-in-part of application No. 09/161,658, filed on Sep. 29, 1998, now Pat. No. 6,237,398, which is a continuation-in-part of application No. 09/000,553, filed on Dec. 30, 1997, now Pat. No. 6,140,740.

(51) Int. Cl.[7] .................................................. A61B 5/00
(52) U.S. Cl. ...................... 600/300; 600/309; 600/500; 128/899
(58) Field of Search ................................ 600/300, 309, 600/310, 323, 339, 500, 502, 504, 505; 128/899, 903; 607/30, 31, 32, 33, 60, 61

(56) References Cited

U.S. PATENT DOCUMENTS

| 4,494,950 A | * | 1/1985 | Fischell ................... 128/903 X |
| 5,620,475 A | * | 4/1997 | Magnusson .................. 607/30 |
| 5,704,352 A | * | 1/1998 | Tremblay et al. ........... 600/300 |
| 5,743,267 A | * | 4/1998 | Nikolic et al. ........... 128/903 X |
| 5,749,909 A | * | 5/1998 | Schroeppel et al. ........... 607/33 |
| 5,807,258 A | * | 9/1998 | Cimochowski et al. . 600/504 X |
| 5,891,180 A | * | 4/1999 | Greeninger et al. ........... 607/32 |
| 5,967,989 A | * | 10/1999 | Cimochowski et al. ..... 600/459 |
| 6,015,387 A | * | 1/2000 | Schwartz et al. ........... 600/504 |
| 6,170,488 B1 | * | 1/2001 | Spillman, Jr. et al. ...... 128/899 |
| 6,198,963 B1 | * | 3/2001 | Haim et al. .................. 600/424 |

* cited by examiner

*Primary Examiner*—Eric F. Winakur
*Assistant Examiner*—Joseph A. Cadugan
(74) *Attorney, Agent, or Firm*—G. E. Ehrlich Ltd.

(57) ABSTRACT

An implantable biosensor system for monitoring and optionally alleviating a physiological condition in a patient is provided and includes (a) at least one sensor for sensing at least one parameter of a physiological condition and for generating electrical sensor signals representative of the physiological condition; and (b) a first acoustic activatable transducer being directly or indirectly coupled with the at least one sensor, the first acoustic activatable transducer being for converting a received acoustic interrogation signal from outside the patient's body into an electrical power for energizing the processor, the first acoustic activatable transducer further being for converting the electrical sensor signals of the at least one sensor into acoustic signals receivable out of the patient's body, such that information pertaining to the at least one parameter of the physiological condition can be relayed outside the patient's body upon generation of an acoustic interrogation signal.

3 Claims, 11 Drawing Sheets

IMPLANTABLE ACOUSTIC BIO-SENSING SYSTEM AND METHOD

This is a continuation-in-part of U.S. patent application Ser. No. 09/161,658, filed Sep. 29, 1998, now U.S. Pat. No. 6,237,398, issued May 29, 2001, which is a continuation-in-part of U.S. patent application Ser. No. 09/000,553, filed Dec. 30, 1997, now U.S. Pat. No. 6,140,740, issued Oct. 31, 2000.

FIELD AND BACKGROUND OF THE INVENTION

The present invention relates to a biosensing system and method for monitoring internal physiological conditions of a patient. More particularly, the present invention relates to a biosensor system implantable in a patient's body that includes at least one sensor, an active acoustic transducer and a miniature processor. The sensor is used to monitor a physiological condition of the patient and relay information pertaining to the physiological condition through the miniature processor to the active acoustic transducer. The active acoustic transducer transmits this information out of the patient's body as an acoustic signal. Transmission of an acoustic signal from the transducer is triggered by an externally generated acoustic interrogation and energizing signal, which is produced by a second acoustic transducer positioned externally, yet in intimate contact with, the patient's body. The miniature electronic processor is utilized for the various required functions such as conditioning, digitization and amplification of the sensor signals. The biosensor of the present invention can also include a shunt and a monitoring device embedded in the walls of the shunt for permitting identification and non-invasive testing of the operation of the shunt via the acoustic transducer.

Many medical conditions require the monitoring and measurement of internal physiological conditions of a patient. For example, hydrocephalus, which is a brain condition where cerebrospinal fluid accumulates at abnormally high pressures in ventricles or chambers of a patient's brain, may require monitoring of the intra-cranial fluid pressure of the patient.

Implantable devices for monitoring internal physiological conditions of a patient are known in the art. One such prior art device includes an implantable pressure sensor that transmits pressure signals out of the patient by mechanism of a wire or contact passing through the patient's skull (see, for example, U.S. Pat. No. 4,677,985). These types of devices are generally unsatisfactory due to increased risk of infection and patient discomfort caused by the externally extending wire.

Monitoring devices that are completely implantable within a patient are also known in the art. One such prior art devices is described in U.S. Pat. No. 4,471,786 and includes a sensor for sensing a physiological condition of the patient and a transmitter and battery assembly for transmitting the sensor signals out of the patient's body. These types of devices are also unsatisfactory for many types of medical conditions since the batteries are bulky and must be periodically replaced, thus necessitating additional surgery.

Implantable monitoring devices that do not require batteries have also been developed. Such devices (see, for example, U.S. Pat. Nos. 3,943,915 and 4,593,703) employ sensors coupled with frequency tuned Lumped-Constant (L-C) circuits. The sensors mechanically translate changes in sensed physiological condition to the inductor or capacitor of the tuned L-C circuit for changing the reactance of the L-C circuit. This change in reactance alters the resonant frequency of the circuit, which is then detected by an external receiver and converted to a signal representative of the monitored physiological condition.

Although these L-C type implantable monitoring devices are superior to battery operated devices in some respects, they also suffer from several limitations that limit their utility. For example, the L-C circuits are difficult to calibrate once implanted, are inherently single-channel, and are only sensitive in a particular range of measurements. Thus, L-C type monitoring devices are not always accurate after they have been implanted for a long period of time and are not suitable for use with sensors that have a wide sensing range. In addition, no processing power is provided.

Another implantable monitoring device that does not utilizes wire connection or a battery supply makes use of large electromagnetic antennae to provide the energy required for the data processing inside the body. These antennas are big and risky to implant. Also, due to the high absorption of electromagnetic energy by human tissue, only subcutaneous implants are used, and energy into the depth of the body is realized by wiring coupling. Only small amounts of electromagnetic energy can be transmitted from an external antenna directly to a monitoring device deep in the body.

A general limitation of all of the above-described prior art implantable monitoring devices is that they are operable for sensing or monitoring only one physiological condition. Thus, if a doctor wishes to monitor, e.g., both the pressure and the temperature of the fluid in the ventricles of a patient's brain, two such devices must be implanted.

Furthermore, these prior art implantable devices merely monitor a physiological condition of the patient and transmit a signal representative of the condition out of the patient's body, but do not perform any processing or conversion of the signals.

In addition, due to inherent design limitations, these devices cannot be utilized for alleviating the underlying cause of the physiological condition monitored. For example, intra-cranial pressure sensors designed for use with patients suffering from hydrocephalus merely detect when fluid pressure levels within the patient's brain are high, but are not operable for reducing the amount of cerebrospinal fluid accumulated in the patient's brain. Thus, once these prior intra-cranial pressure sensors determine that the pressure in the patient's brain is too high, surgery must be performed to alleviate the condition.

An improved implantable biosensor for monitoring and alleviating internal physiological condition such as intracranial pressure has been described in U.S. Pat. No. 5,704,352 which discloses a biosensor system which includes at least one sensor for monitoring a physiological condition of the patient and a passive radio frequency transducer that receives sensor signals from the sensor or sensors, digitizes the sensor signals, and transmits the digitized signals out of the patient's body when subjected to an externally generated electromagnetically interrogation and energizing signal. The biosensor system described also includes a shunt, and as such it can be used for alleviating intracranial pressure monitored by the sensors of the biosensor.

Although this biosensor system presents a major advance over the above mentioned prior art devices and systems, it suffers from limitations inherent to the radio frequency transducer utilized thereby. Since this transducer requires the use of an antenna to receive and transmit signals, it posses limited reception and transmission capabilities due to the directional nature of such antennas. In addition, due to the high absorption of electromagnetic energy by human tissue, deeply embedded implants cannot be realized by this system and as a result, the intra body positioning of such a biosensor is limited to regions close to the skin which are accessible to electromagnetic signals, thus greatly limiting the effectiveness of such a system.

There is thus a widely recognized need for, and it would be highly advantageous to have, a biosensor system for monitoring and alleviating internal physiological conditions, such as intra-cranial pressure, devoid of the above limitations.

SUMMARY OF THE INVENTION

It is therefore an object of the present invention to provide a biosensor which can be used for non-invasive monitoring of body parameters.

It is another object of the present invention to provide such a biosensor which does not require wiring or an integral power source.

It is yet another object of the present invention to provide a biosensor which is less sensitive to extracorporeal positional effect when energized as compared to prior art devices.

It is still another object of the present invention to provide a biosensor which is effectively operable from any depth within the body.

To realize and reduce down to practice these objectives, the biosensor according to the present invention takes advantage of the reliable conductivity of acoustic radiation within water bodies, such as a human body and of an acoustic activatable piezoelectric transducer. According to one aspect of the present invention there is provided According to one aspect of the present invention there is provided an implantable biosensor system for monitoring and optionally alleviating a physiological condition in a patient, the biosensor system comprising (a) at least one sensor for sensing at least one parameter of a physiological condition and for generating electrical sensor signals representative of the physiological condition; and (b) a first acoustic activatable transducer being directly or indirectly coupled with the at least one sensor, the first acoustic activatable transducer being for converting a received acoustic interrogation signal from outside the patient's body into an electrical power for energizing the processor, the first acoustic activatable transducer further being for converting the electrical sensor signals of the at least one sensor into acoustic signals receivable out of the patient's body, such that information pertaining to the at least one parameter of the physiological condition can be relayed outside the patient's body upon generation of an acoustic interrogation signal.

According to further features in preferred embodiments of the invention described below, the biosensor system further comprising a processor coupling between the at least one sensor and the first acoustic activatable transducer, the processor being for converting the electrical sensor signals into converted electrical signals representative of the physiological condition, the processor being energized via the electrical power.

According to another aspect of the present invention there is provided an implantable biosensor system for monitoring and alleviating a physiological condition in a patient, the biosensor system comprising (a) a shunt having a fluid passageway and being operable for draining fluid through the fluid passageway from a portion of a patient's body; (b) a monitoring and operating mechanism coupled with the shunt for non-invasively monitoring the physiological condition and operating the shunt, the monitoring and operating mechanism including at least one sensor for sensing at least one parameter of the physiological condition and for generating electrical sensor signals representative of the physiological condition; and (c) a first acoustic activatable transducer being directly or indirectly coupled with the at least one sensor, the first acoustic activatable transducer being for converting a received acoustic interrogation signal from outside the patient's body into an electrical power for energizing the at least one sensor and for operating the shunt upon command, the first acoustic activatable transducer further being for converting the electrical sensor signals into acoustic signals receivable out of the patient's body, such that information pertaining to the at least one parameter of the physiological condition can be relayed outside the patient's body upon generation of an acoustic interrogation signal and the shunt is operable upon command.

According to still further features in the described preferred embodiments the monitoring and operating mechanism further includes a processor coupled with the at least one sensor, the processor serves for converting the electrical sensor signals to converted electrical signals representative of the physiological condition.

According to still further features in the described preferred embodiments the command is an acoustic operation signal provided from outside the body.

According to still further features in the described preferred embodiments the shunt is a cerebrospinal fluid shunt for draining cerebrospinal fluid from the patient's brain.

According to still further features in the described preferred embodiments the at least one sensor includes a first pressure sensor positioned within the fluid passageway for sensing the pressure of the cerebrospinal fluid in the patient's brain and for generating a first pressure signal representative of that pressure.

According to still further features in the described preferred embodiments the at least one pressure sensor includes a second pressure sensor positioned at a distance from the first pressure sensor and being for sensing the pressure of the cerebrospinal fluid when flowing through the shunt and for generating a second pressure signal representative of that pressure.

According to still further features in the described preferred embodiments the processor receives the first and second pressure signals from the first and second pressure sensors and calculates the flow rate of cerebrospinal fluid through the shunt.

According to still further features in the described preferred embodiments the first acoustic activatable transducer includes (i) a cell member having a cavity; (ii) a substantially flexible piezoelectric layer attached to the cell member, the piezoelectric layer having an external surface and an internal surface, the piezoelectric layer featuring such dimensions so as to enable fluctuations thereof at its resonance frequency upon impinging of the acoustic interrogation signal; and (iii) a first electrode attached to the external surface and a second electrode attached to the internal surface.

According to still further features in the described preferred embodiments the piezoelectric layer is of a material selected from the group consisting of PVDF and piezoceramic.

According to still further features in the described preferred embodiments the processor includes a conditioner and a digitizer for converting the electrical sensor signal to the converted electrical signal.

According to still further features in the described preferred embodiments the converted electrical signal is a digital signal.

According to still further features in the described preferred embodiments the processor, the first acoustic activatable transducer and the at least one sensor are co-integrated into a single biosensor device.

According to still further features in the described preferred embodiments the biosensor system further comprising (c) an extracorporeal station positionable against the patient's body the extracorporeal station including an interrogation signal generator for generating the acoustic interrogation signal, the interrogation signal generator including at least one second transducer for transmitting the interrogation signal to the first acoustic activatable transducer and for receiving the receivable acoustic signals from the first acoustic activatable transducer.

According to still further features in the described preferred embodiments the processor includes a memory device for storing the electrical sensor signals and an analyzer for analyzing the electrical sensor signals.

According to still further features in the described preferred embodiments the processor includes a programmable microprocessor.

According to still further features in the described preferred embodiments the at least one sensor is selected from the group consisting of a pressure sensor, a temperature sensor, a pH sensor, a blood sugar sensor, a blood oxygen sensor, a motion sensor, a flow sensor, a velocity sensor, an acceleration sensor, a force sensor, a strain sensor, an acoustics sensor, a moisture sensor, an osmolarity sensor, a light sensor, a turbidity sensor, a radiation sensor, an electromagnetic field sensor, a chemical sensor, an ionic sensor, and an enzymatic sensor.

According to still further features in the described preferred embodiments the first acoustic activatable transducer is capable of transmitting an identification code identifying the transducer.

According to yet another aspect of the present invention there is provided a method for non-invasive monitoring of a physiological condition within a patient's body, the method comprising the steps of (a) sensing at least one parameter associated with the physiological condition via at least one sensor implanted within the patient's body to thereby obtain information pertaining to the physiological condition as an electrical output; (b) converting the electrical output into an acoustic signal via an acoustic transducer and thereby acoustically relaying the information to outside the patient's body; and (c) relaying an acoustic interrogation signal from outside the patient's body for activating the at least one sensor.

According to still another aspect of the present invention there is provided a method for non-invasive monitoring and alleviating of a physiological condition within a patient's body, the method comprising the steps of (a) sensing at least one parameter associated with the physiological condition via at least one sensor implanted within the patient's body to thereby obtain information pertaining to the physiological condition as an electrical output; (b) converting the electrical output into an acoustic signal via an acoustic transducer and thereby acoustically relaying the information to outside the patient's body; and (c) relaying an acoustic interrogation signal from outside the patient's body for activating the at least one sensor and further for activating a shunt for alleviating the physiological condition.

The present invention successfully addresses the shortcomings of the presently known configurations by providing a biosensor which can be used for non-invasive monitoring of body parameters, which does not require wiring, which does not require an integral power source, which can be effectively positioned at any location and depth within the body and which is much less subject to interrogation positional effect as compared with prior art devices.

BRIEF DESCRIPTION OF THE DRAWINGS

The invention is herein described, by way of example only, with reference to the accompanying drawings, wherein:

FIG. 2a is a cross section of a transducer element according to the present invention taken along line C—C in FIG. 1a;

FIG. 2b is a cross section of a transducer element according to the present invention taken along line D—D in FIG. 1a;

FIG. 2c is a cross section of a transducer element according to the present invention taken along line E—E in FIG. 1a;

FIG. 2d is a cross section of a transducer element according to the present invention taken along line F—F in FIG. 1a;

FIG. 2e is a cross section of a transducer element according to the present invention taken along line G—G in FIG. 1a;

DESCRIPTION OF THE PREFERRED EMBODIMENTS

Figure 1A:
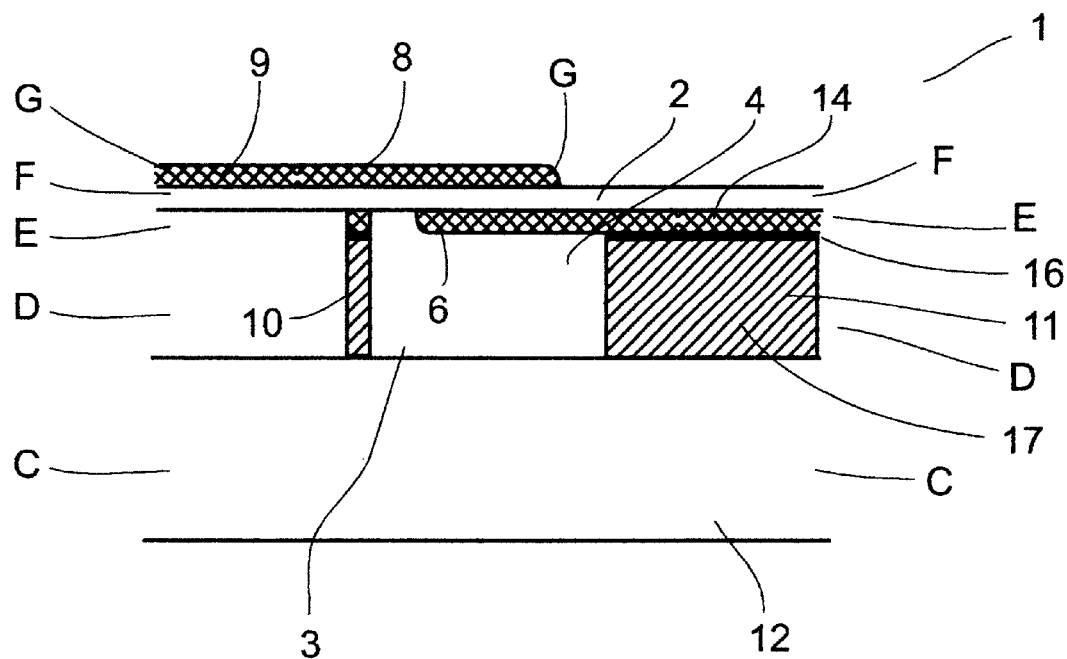
FIG. 1a is a longitudinal cross section of a transducer element according to the present invention taken along lines A—A in FIGS. 2a–2e.

The present invention is of an intrabody bio-sensing system and method which can be used for both monitoring and alleviating physiological conditions within a patient's body. Specifically, the biosensor system and method of the present invention incorporates an active acoustic transducer communicating with sensors and optionally with a shunt implanted within the patient's body for monitoring and alleviating, for example, intra-cranial pressure of a patient suffering from hydrocephalus.

The principles and operation of an implantable biosensor system according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting. For purposes of better understanding the system and method according to the present invention, as illustrated in FIGS. 10–14 of the drawings, reference is first made to the construction and operation of a transducer as described in U.S. patent application Ser. No. 09/000,553.

Referring now to the drawings, FIGS. 1a, 1b and 2a–2e illustrate a preferred embodiment of a transducer element according to the present invention which is referred to herein as transducer element 1. Transducer element 1 serves for converting received acoustic signals into electrical power and for converting electrical power to transmitted acoustic signals. As shown in the figures, the transducer element 1 includes at least one cell member 3 including a cavity 4 etched into a substrate and covered by a substantially flexible piezoelectric layer 2. Attached to piezoelectric layer 2 are an upper electrode 8 and a lower electrode 6, the electrodes for connection to an electronic circuit.

The substrate is preferably made of an electrical conducting layer 11 disposed on an electrically insulating layer 12, such that cavity 4 is etched substantially through the thickness of electrically conducting layer 11.

Electrically conducting layer 11 is preferably made of copper and insulating layer 12 is preferably made of a polymer such as polyimide. Conventional copper-plated polymer laminate such as KAPTON™ sheets may be used for the production of transducer element 1. Commercially available laminates such as NOVACLAD™ may be used. Alternatively, the substrate may include a silicon layer, or any other suitable material. Alternatively, layer 11 is made of a non-conductive material such as PYRALIN™.

Preferably, cavity 4 is etched into the substrate by using conventional printed-circuit photolithography methods. Alternatively, cavity 4 may be etched into the substrate by using VLSI/micro-machining technology or any other suitable technology.

Piezoelectric layer 2 may be made of PVDF or a copolymer thereof. Alternatively, piezoelectric layer 2 is made of a substantially flexible piezoceramic. Preferably, piezoelectric layer 2 is a poled PVDF sheet having a thickness of about 9–28 μm. Preferably, the thickness and radius of flexible layer 2, as well as the pressure within cavity 4, are specifically selected so as to provide a predetermined resonant frequency. When using the embodiment of FIGS. 1a and 1b, the radius of layer 2 is defined by the radius of cavity 4.

By using a substantially flexible piezoelectric layer 2, the invention described in U.S. patent application Ser. No. 09/000,553 allows to provide a miniature transducer element whose resonant frequency is such that the acoustic wavelength is much larger than the extent of the transducer. This enables the transducer to be omnidirectional even at resonance, and further allows the use of relatively low frequency acoustic signals which do not suffer from significant attenuation in the surrounding medium.

Prior art designs of miniature transducers, however, rely on rigid piezoceramic usually operating in thickness mode. In such cases the resonant frequency relates to the size of the element and speed of sound in the piezoceramic, and is higher by several orders of magnitude.

The invention described in U.S. patent application Ser. No. 09/000,553 provides a transducer which is omnidirectional, i.e., insensitive to the direction of the impinging acoustic rays, thereby substantially simplifying the transducer's operation relative to other resonant devices. Such a transducer element is thus suitable for application in confined or hidden locations, where the orientation of the transducer element cannot be ascertained in advance.

According to a specific embodiment, cavity 4 features a circular or hexagonal shape with radius of about 200 μm. Electrically conducting layer 11 preferably has a thickness of about 15 μm. Cell member 3 is preferably etched completely through the thickness of electrically conducting layer 11. Electrically insulating layer 12 preferably features a thickness of about 50 μm. The precise dimensions of the various elements of a transducer element according to the invention described in U.S. patent application Ser. No. 09/000,553 may be specifically tailored according to the requirements of the specific application.

Cavity 4 preferably includes a gas such as air. The pressure of gas within cavity 4 may be specifically selected so as to predetermine the sensitivity and ruggedness of the transducer as well as the resonant frequency of layer 2.

Figure 2A:
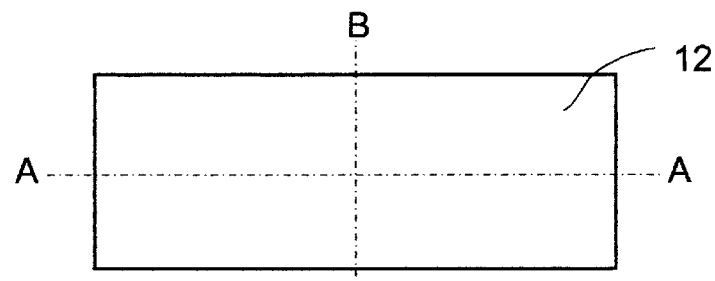
Figure 2B:
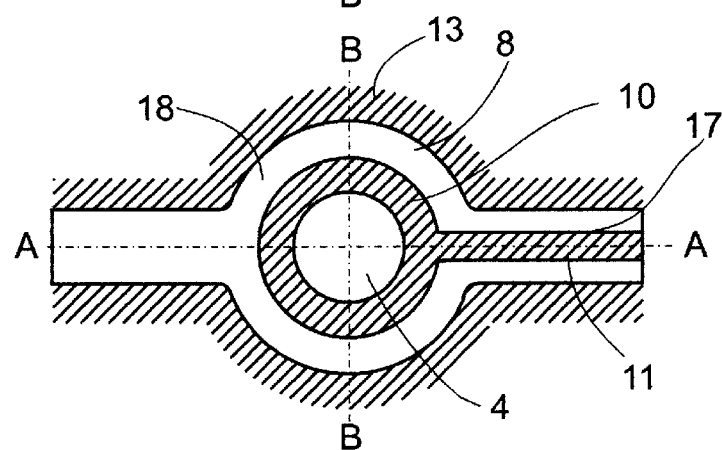

As shown in FIG. 2b, an insulating chamber 18 is etched into the substrate, preferably through the thickness of conducting layer 11, so as to insulate the transducer element from other portions of the substrate which may include other electrical components such as other transducer elements etched into the substrate. According to a specific embodiment, the width of insulating chamber 18 is about 100 μm. As shown, insulating chamber 18 is etched into the substrate so as to form a wall 10 of a predetermined thickness enclosing cavity 4, and a conducting line 17 integrally made with wall 10 for connecting the transducer element to another electronic component preferably etched into the same substrate, or to an external electronic circuit.

Figure 1B:
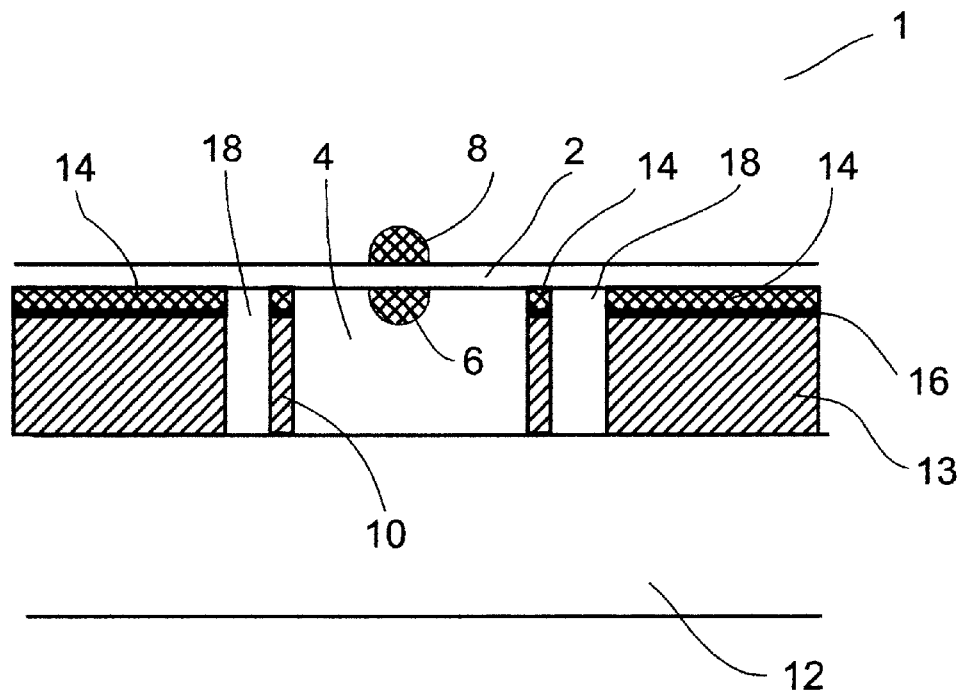
FIG. 1b is a longitudinal cross section of a transducer element according to the present invention taken along lines B—B in FIGS. 2a–2e.
Figure 2C:
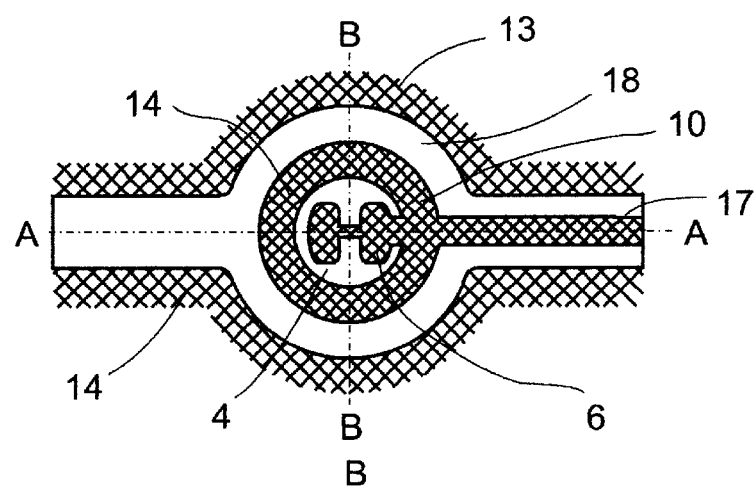
Figure 2D:
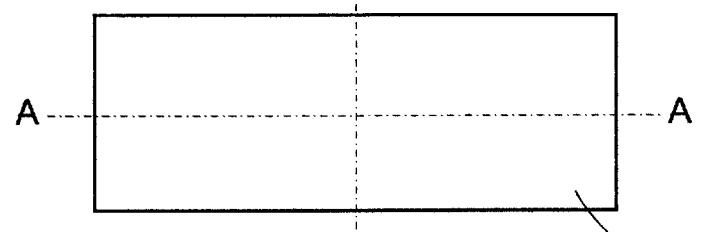
Figure 2E:
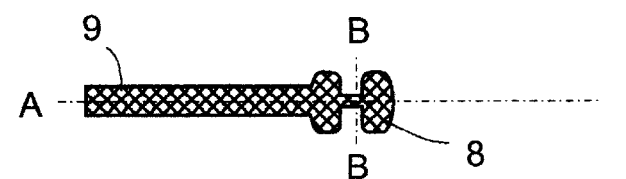

As shown in FIGS. 1a and 1b, attached to piezoelectric layer 2 are upper electrode 8 and lower electrode 6. As shown in FIGS. 2c and 2e, upper electrode 8 and lower electrode 6 are preferably precisely shaped, so as to cover a predetermined area of piezoelectric layer 2. Electrodes 6 and 8 may be deposited on the upper and lower surfaces of piezoelectric membrane 2, respectively, by using various methods such as vacuum deposition, mask etching, painting, and the like.

As shown in FIG. 1a, lower electrode 6 is preferably made as an integral part of a substantially thin electrically conducting layer 14 disposed on electrically conducting layer 11. Preferably, electrically conducting layer 14 is made of a Nickel.Copper alloy and is attached to electrically conducting layer 11 by mechanism of a sealing connection 16. Sealing connection 16 may be made of indium. According to a preferred configuration, sealing connection 16 may feature a thickness of about 10 $\mu$m, such that the overall height of wall 10 of cavity 4 is about 20–25 $\mu$m.

As shown in FIG. 2c, electrically conducting layer 14 covers the various portions of conducting layer 11, including wall 10 and conducting line 17. The portion of conducting layer 14 covering conducting line 17 is for connection to an electronic component, as further detailed hereinunder.

According to a preferred embodiment, electrodes 6 and 8 are specifically shaped to include the most energy-productive region of piezoelectric layer 2, so as to provide maximal response of the transducer while optimizing the electrode area, and therefore the cell capacitance, thereby maximizing a selected parameter such as voltage sensitivity, current sensitivity, or power sensitivity of the transducer element.

The vertical displacement of piezoelectric layer 2, $\Psi$, resulting from a monochromatic excitation at angular frequency $\omega$ is modeled using the standard equation for thin plates:

$$(\nabla^2 - \gamma^2)(\nabla^2 + \gamma^2)\Psi - \frac{3(1-v^2)}{2Qh^3}P + \frac{3iZ\omega(1-v^2)}{2Qh^3}\Psi = 0$$

wherein Q is the Young's modulus representing the elasticity of layer 2; h the half-thickness of layer 2; v is the Poisson ratio for layer 2; $\gamma$ is the effective wavenumber in the layer given by: $\gamma^4 = 3\rho(1-v^2)\omega^2/Qh^2$, wherein $\rho$ is the density of layer 2 and $\omega$ is the angular frequency of the applied pressure (wherein the applied pressure may include the acoustic pressure, the static pressure differential across layer 2 and any other pressure the transducer comes across); Z is the mechanical impedance resulting from the coupling of layer 2 to both external and internal media of cavity 4, wherein the internal medium is preferably air and the external medium is preferably fluid; P is the acoustic pressure applied to layer 2, and $\overline{\Psi}$ represents the average vertical displacement of layer 2.

When chamber 4 is circular, the solution (given for a single frequency component $\omega$) representing the dynamic displacement of a circular layer 2 having a predetermined radius a, expressed in polar coordinates, is:

$$\Psi(r, \varphi) = \frac{I_1(\gamma a)[J_0(\gamma r) - J_0(\gamma a)] + J_1(\gamma a)[I_0(\gamma r) - I_0(\gamma a)]}{2h\rho\omega^2 L_0(\gamma a) + i\omega Z L_2(\gamma a)}P$$

$$L_0(z) = I_o(z)J_1(z) + J_0(z)I_1(z), L_2(z) = J_2(z)I_1(z) - I_2(z)J_1(z)$$

$$Z = \frac{P_A}{i\omega H_A} + i\left[\frac{4}{3\pi} + \frac{1}{6}\right]\omega\rho_W a$$

wherein $\Psi(r,\phi)$ is time-dependent and represents the displacement of a selected point located on circular layer 2, the specific location of which is given by radius r and angle $\phi$; J and I are the normal and modified Bessel functions of the first kind, respectively; $P_A$, $H_A$ are the air pressure within cavity 4 and the height of chamber 4, respectively; and $\rho_W$ is the density of the fluid external to cavity 4.

The first term of the impedance Z relates to the stiffness resulting from compression of air within cavity 4, and the second term of Z relates to the mass added by the fluid boundary layer. An additional term of the impedance Z relating to the radiated acoustic energy is substantially negligible in this example.

The charge collected between electrodes 6 and 8 per unit area is obtained by evaluating the strains in layer 2 resulting from the displacements, and multiplying by the pertinent off-diagonal elements of the piezoelectric strain coefficient tensor, $e_{31}$, $e_{32}$, as follows:

$$Q(r, \varphi, t) = \left(e_{31}\left(\frac{\partial\Psi}{\partial x}\right)\right)^2 + \left(e_{32}\left(\frac{\partial\Psi}{\partial y}\right)\right)^2$$

wherein $Q(r,\phi,t)$ represents the charge density at a selected point located on circular layer 2, the specific location of which is given by radius r and angle $\phi$; x is the stretch direction of piezoelectric layer 2; y is the transverse direction (the direction perpendicular to the stretch direction) of layer 2; $e_{31}$, $e_{32}$ are off-diagonal elements of the piezoelectric strain coefficient tensor representing the charge accumulated at a selected point on layer 2 due to a given strain along the x and y directions, respectively, which coefficients being substantially dissimilar when using a PVDF layer. $\Psi$ is the displacement of layer 2, taken as the sum of the displacement for a given acoustic pressure P at frequency f, and the static displacement resulting from the pressure differential between the interior and exterior of cavity 4, which displacements being extractable from the equations given above.

The total charge accumulated between electrodes 6 and 8 is obtained by integrating $Q(r,\phi,t)$ over the entire area S of the electrode:

$$Q = \int_S Q(r, \varphi, t)d\vec{x}$$

The capacitance C of piezoelectric layer 2 is given by:

$$C = \frac{\varepsilon}{2h}\int_S d\vec{x},$$

wherein $\in$ is the dielectric constant of piezoelectric layer 2; and 2 h is the thickness of piezoelectric layer 2.

Accordingly, the voltage, current and power responses of piezoelectric layer 2 are evaluated as follows:

$$V = \frac{2h\int_S Q(r, \varphi, t)d\vec{x}}{\varepsilon\int_S d\vec{x}}, I = 2i\omega\int_S Q(r, \varphi, t)d\vec{x},$$

$$W = \frac{4ih\left[\int_S Q(r, \varphi, t)d\vec{x}\right]^2}{\varepsilon\int_S d\vec{x}}$$

The DC components of Q are usually removed prior to the evaluation, since the DC currents are usually filtered out. The values of Q given above represent peak values of the AC components of Q, and should be modified accordingly so as to obtain other required values such as RMS values.

According to the above, the electrical output of the transducer expressed in terms of voltage, current and power responses depend on the AC components of Q, and on the shape S of the electrodes. Further, as can be seen from the above equations, the voltage response of the transducer may be substantially maximized by minimizing the area of the electrode. The current response, however, may be substantially maximized by maximizing the area of the electrode.

Figure 3:
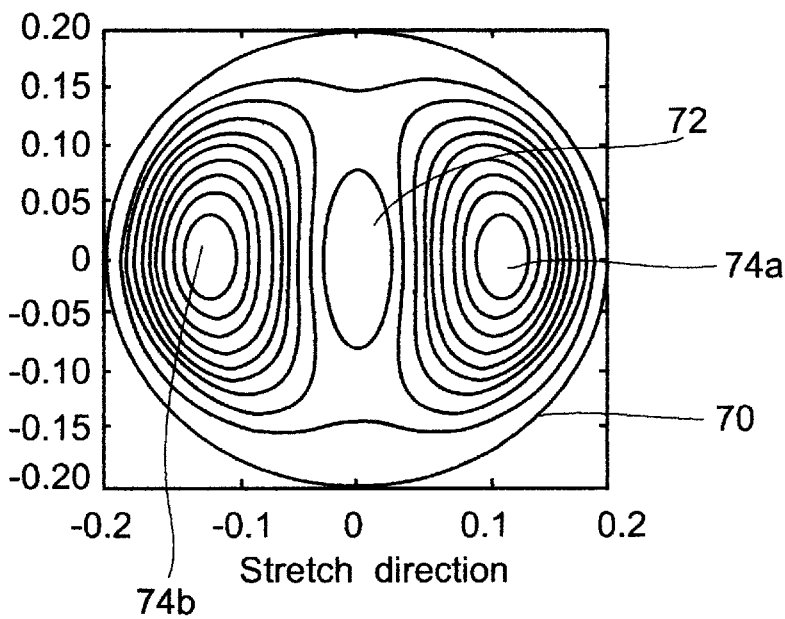
FIG. 3 shows the distribution of charge density across a piezoelectric layer of a transducer element resulting from the application of a constant pressure over the entire surface of the layer.
Figure 4A:
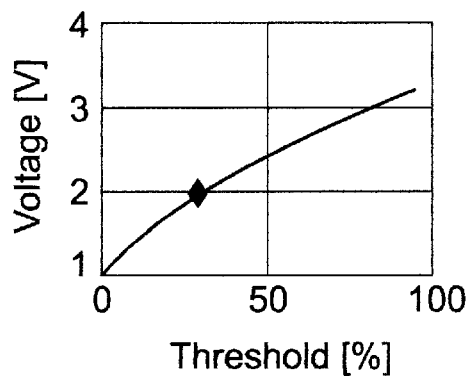
FIG. 4 shows the results of optimization performed for the power response of a transducer according to the present invention.
Figure 4C:
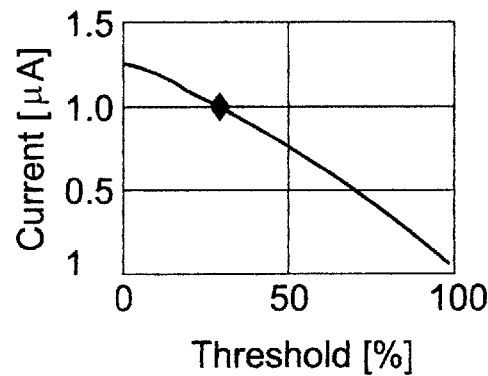
Figure 4B:
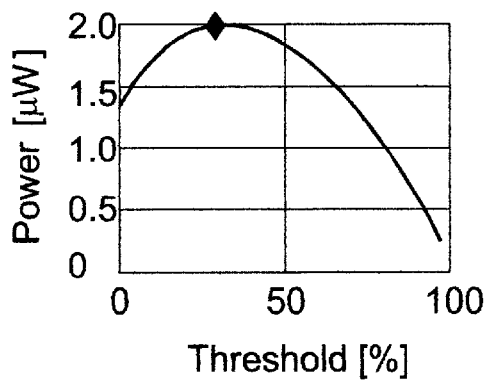
Figure 4D:
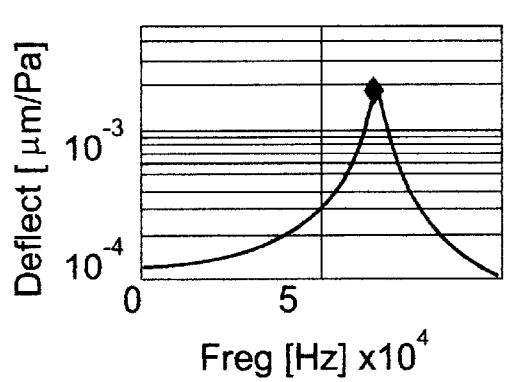

FIG. 3 shows the distribution of charge density on a circular piezoelectric layer 2 obtained as a result of pressure (acoustic and hydrostatic) applied uniformly over the entire area of layer 2, wherein specific locations on layer 2 are herein defined by using Cartesian coordinates including the stretch direction (x direction) and the transverse direction (y direction) of layer 2. It can be seen that distinct locations on layer 2 contribute differently to the charge density. The charge density vanishes at the external periphery 70 and at the center 72 of layer 2 due to minimal deformation of these portions. The charge density is maximal at two cores 74a and 74b located symmetrically on each side of center 72 due to maximal strains (in the stretch direction) of these portions.

A preferred strategy for optimizing the electrical responses of the transducer is to shape the electrode by selecting the areas contributing at least a selected threshold percentage of the maximal charge density, wherein the threshold value is the parameter to be optimized. A threshold value of 0% relates to an electrode covering the entire area of layer 2.

FIG. 4 shows the results of an optimization performed for the power response of a transducer having a layer 2 of a predetermined area. As shown in the Figure, the threshold value which provides an optimal power response is about 30% (graph b). Accordingly, an electrode which covers only the portions of layer 2 contributing at least 30% of the maximal charge density yields a maximal power response. The pertinent voltage response obtained by such an electrode is higher by a factor of 2 relative to an electrode completely covering layer 2 (graph a). The current response obtained by such electrode is slightly lower relative to an electrode completely covering layer 2 (graph c). Further as shown in the Figure, the deflection of layer 2 is maximal when applying an acoustic signal at the resonant frequency of layer 2 (graph d).

Figure 5:
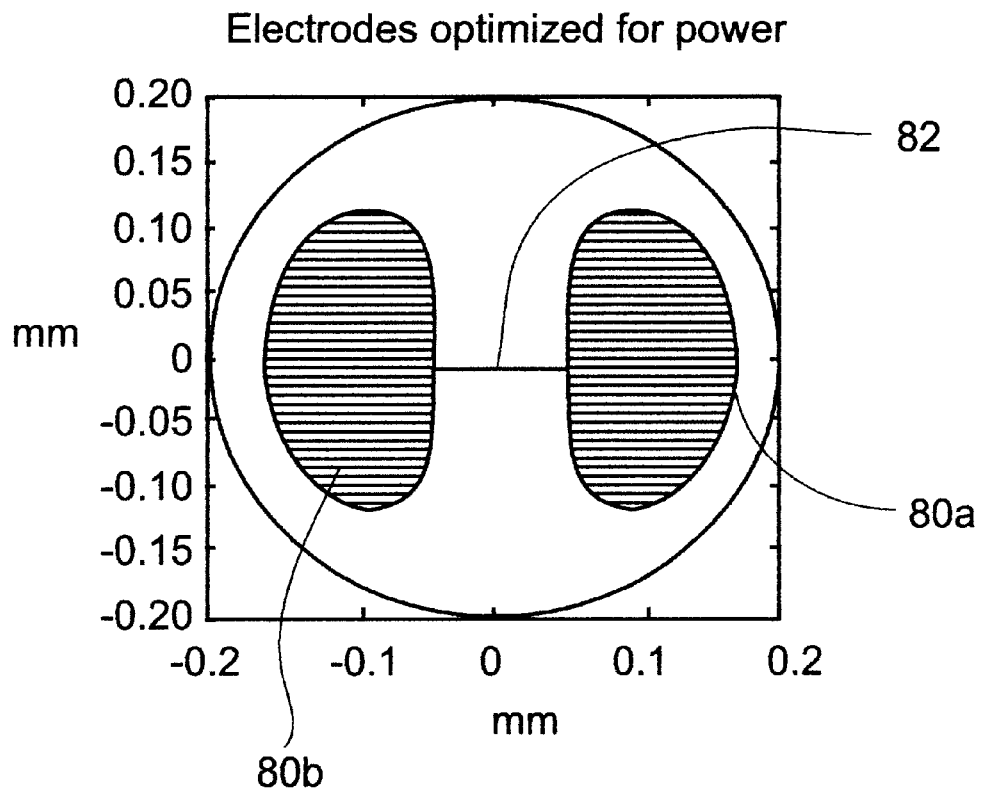
FIG. 5 shows a preferred electrode shape for maximizing the power response of a transducer according to the present invention.

A preferred electrode shape for maximizing the power response of the transducer is shown in FIG. 5, wherein the electrode includes two electrode portions 80a and 80b substantially covering the maximal charge density portions of layer 2, the electrode portions being interconnected by mechanism of a connecting member 82 having a minimal area. Preferably, portions 80a and 80b cover the portions of layer 2 which yield at least a selected threshold (e.g. 30%) of the maximal charge density.

According to the present invention any other parameter may be optimized so as to determine the shape of electrodes 6 and 8. According to further features of the invention described in U.S. patent application Ser. No. 09/000,553, only one electrode (upper electrode 8 or lower electrode 6) may be shaped so as to provide maximal electrical response of the transducer, with the other electrode covering the entire area of layer 2. Since the charge is collected only at the portions of layer 2 received between upper electrode 8 and lower electrode 6, such configuration is operatively equivalent to a configuration including two shaped electrodes having identical shapes.

Figure 6:
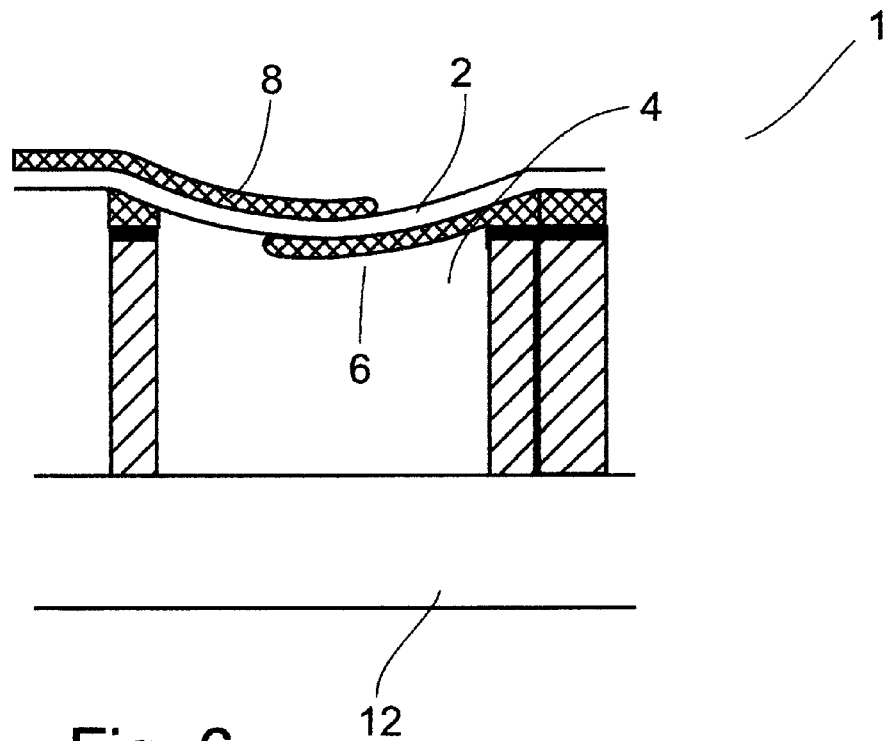
FIG. 6 is a longitudinal section of another embodiment of a transducer element according to the present invention capable of functioning as a transmitter.

Referring now to FIG. 6, according to another embodiment chamber 4 of transducer element 1 may contain gas of substantially low pressure, thereby conferring a substantially concave shape to piezoelectric membrane 2 at equilibrium. Such configuration enables to further increase the electrical response of the transducer by increasing the total charge obtained for a given displacement of layer 2. The total displacement in such an embodiment is given by: $\Psi = P_0 \Psi_{DC} + P \Psi_{AC} \cos \omega t$, wherein $P_0$ is the static pressure differential between the exterior and the interior of cavity 4; $\Psi_{DC}$ is the displacement resulting from $P_0$; P is the amplitude of the acoustic pressure; and $\Psi_{AC}$ is the displacement resulting from P.

Accordingly, the strain along the x direction includes three terms as follows:

$$S_{xx} = \left(\frac{\partial \Psi}{\partial x}\right)^2 = P_0^2 \left(\frac{\partial \Psi_{DC}}{\partial x}\right)^2 + P^2 \left(\frac{\partial \Psi_{AC}}{\partial x}\right)^2 \cos^2 \omega t + 2 P_0 P \frac{\partial \Psi_{DC}}{\partial x} \frac{\partial \Psi_{AC}}{\partial x} \cos \omega t$$

wherein the DC component is usually filtered out.

Thus, by decreasing the pressure of the medium (preferably air) within cavity 4 relative to the pressure of the external medium (preferably fluid), the value of $P_0$ is increased, thereby increasing the value of the third term of the above equation.

Such embodiment makes it possible to increase the charge output of layer 2 for a given displacement, thereby increasing the voltage, current and power responses of the transducer without having to increase the acoustic pressure P. Furthermore, such embodiment enables to further miniaturize the transducer since the same electrical response may be obtained for smaller acoustic deflections. Such embodiment is substantially more robust mechanically and therefore more durable than the embodiment shown in FIGS. 1a and 1b. Such further miniaturization of the transducer enables to use higher resonance frequencies relative to the embodiment shown in FIGS. 1a and 1b.

Preferably, a transducer element 1 according to the invention described in U.S. patent application Ser. No. 09/000,553 is fabricated by using technologies which are in wide use in the microelectronics industry, so as to allow integration thereof with other conventional electronic components as further detailed hereinunder. When the transducer element includes a substrate such as Copper-polymer laminate or silicon, a variety of conventional electronic components may be fabricated onto the same substrate.

According to a preferred embodiment, a plurality of cavities 4 may be etched into a single substrate 12 and covered by a single piezoelectric layer 2, so as to provide a transducer element including a matrix of transducing cell members 3, thereby providing a larger energy collecting area of predetermined dimensions, while still retaining the advantage of miniature individual transducing cell members 3. When using such configuration, the transducing cell members 3 may be electrically interconnected in parallel or serial connections, or combinations thereof, so as to tailor the voltage and current response of the transducer. Parallel connections are preferably used so as to increase the current output while serial connections are preferably used so as to increase the voltage output of the transducer.

Furthermore, piezoelectric layer 2 may be completely depolarized and then repolarized at specific regions thereof, so as to provide a predetermined polarity to each of the transducing cell members 3. Such configuration enables to reduce the complexity of interconnections between cell members 3.

A transducer element according to the invention described in U.S. patent application Ser. No. 09/000,553 may be further used as a transmitter for transmitting information to a remote receiver by modulating the reflection of an external impinging acoustic wave arrived from a remote transmitter.

Referring to FIG. 6, the transducer element shown may function as a transmitter element due to the asymmetric fluctuations of piezoelectric layer 2 with respect to positive and negative transient acoustic pressures obtained as a result of the pressure differential between the interior and exterior of cavity 4.

A transmitter element according to the present invention preferably modulates the reflection of an external impinging acoustic wave by mechanism of a switching element connected thereto. The switching element encodes the information that is to be transmitted, such as the output of a sensor, thereby frequency modulating a reflected acoustic wave.

Such configuration requires very little expenditure of energy from the transmitting module itself, since the acoustic wave that is received is externally generated, such that the only energy required for transmission is the energy of modulation.

Specifically, the reflected acoustic signal is modulated by switching the switching element according to the frequency of a message electric signal arriving from another electronic component such as a sensor, so as to controllably change the mechanical impedance of layer 2 according to the frequency of the message signal.

Preferably, a specific array of electrodes connected to a single cell member or alternatively to a plurality of cell members are used, so as to control the mechanical impedance of layer 2.

Figure 7A:
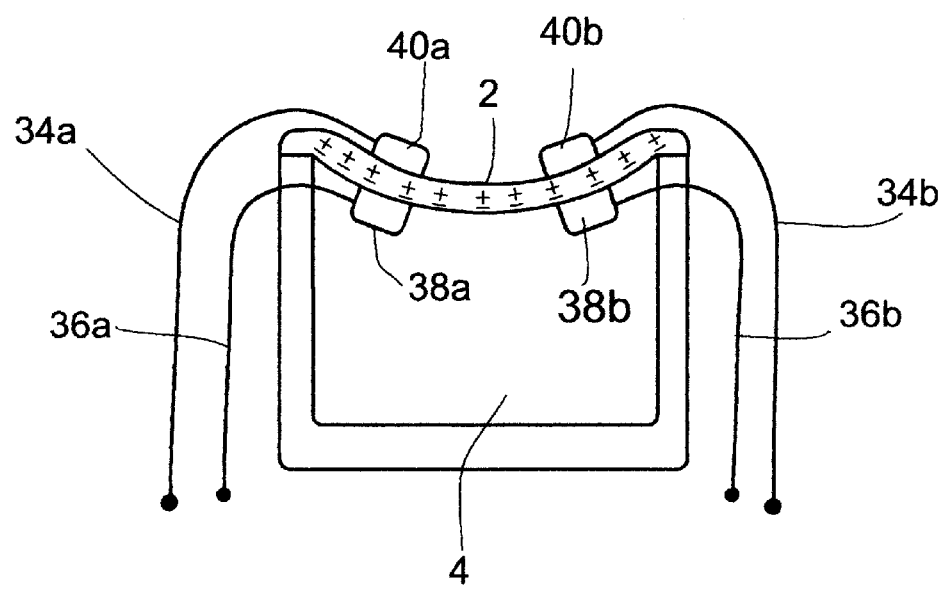
FIGS. 7a–7f are schematic views of possible configurations of transmitters according to the present invention including parallel and anti-parallel electrical connections for controllably changing the mechanical impedance of the piezoelectric layer.

FIGS. 7a–7g illustrate possible configurations for controllably change the impedance of layer 2 of a transmitter element. Referring to FIG. 7a, a transmitter element according to the invention described in U.S. patent application Ser. No. 09/000,553 may include a first and second pairs of electrodes, the first pair including an upper electrode 40a and a lower electrode 38a, and the second pair including an upper electrode 40b and a lower electrode 38b. Electrodes 38a, 38b, 40a and 40b are electrically connected to an electrical circuit by mechanism of conducting lines 36a, 36b, 34a and 34b, respectively, the electrical circuit including a switching element (not shown), so as to alternately change the electrical connections of conducting lines 36a, 36b, 34a and 34b.

Preferably, the switching element switches between a parallel connection and an anti-parallel connection of the electrodes. A parallel connection decreases the mechanical impedance of layer 2, wherein an anti-parallel connection increases the mechanical impedance of layer 2. An anti-parallel connection may be obtained by interconnecting line 34a to 36b and line 34b to 36a. A parallel connection may be obtained by connecting line 34a to 34b and line 36a to 36b. Preferably, the switching frequency equals the frequency of a message signal arriving from an electrical component such as a sensor as further detailed hereinunder.

Figures 7B, 7C:
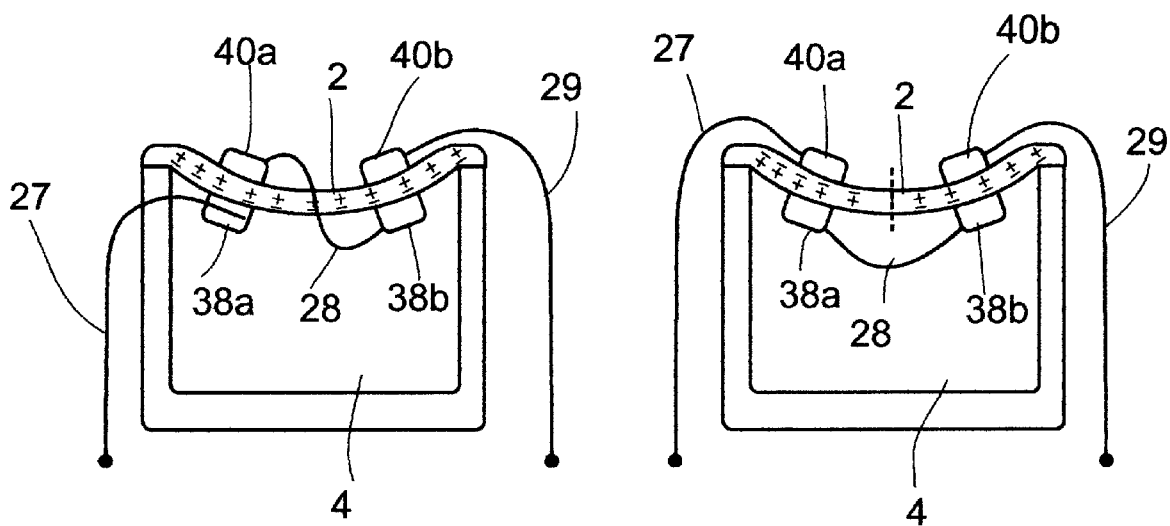

According to another embodiment shown in FIG. 7b, upper electrode 40a is connected to lower electrode 38b by mechanism of a conducting line 28, and electrodes 38a and 40b are connected to an electrical circuit by mechanism of conducting lines 27 and 29, respectively, wherein the electrical circuit further includes a switching element. Such configuration provides an anti-parallel connection of the electrodes, wherein the switching element functions as an on/off switch, thereby alternately increasing the mechanical impedance of layer 2.

In order to reduce the complexity of the electrical connections, layer 2 may be depolarized and then repolarized at specific regions thereof. As shown in FIG. 7c, the polarity of the portion of layer 2 received between electrodes 40a and 38a is opposite to the polarity of the portion of layer 2 received between electrodes 40b and 38b. An anti-parallel connection is thus achieved by interconnecting electrodes 38a and 38b by mechanism of a conducting line 28, and providing conducting lines 27 and 29 connected to electrodes 40a and 40b, respectively, the conducting lines for connection to an electrical circuit including a switching element.

According to another embodiment, the transmitting element includes a plurality of transducing cell members, such that the mechanical impedance of layer 2 controllably changed by appropriately interconnecting the cell members.

Figure 7D:
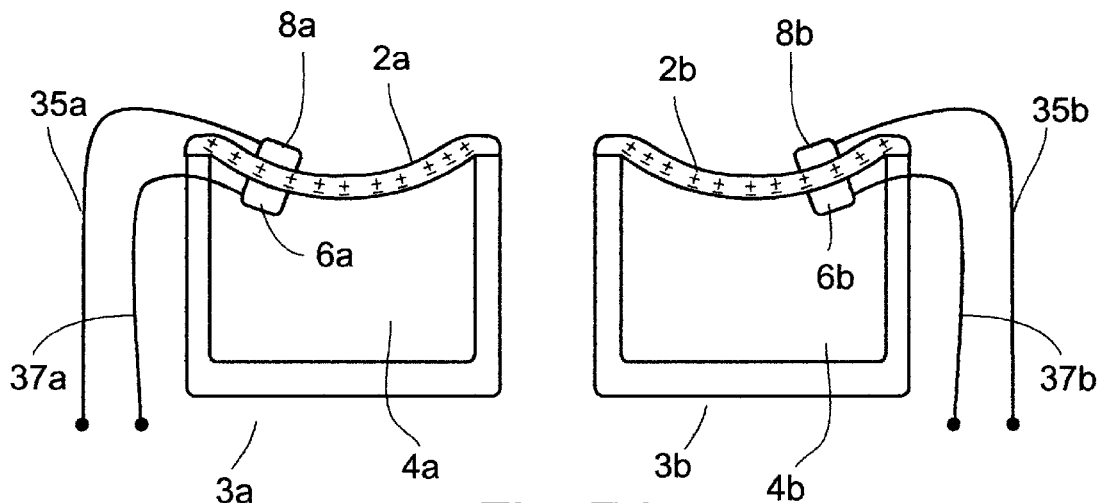

As shown in FIG. 7d, a first transducing cell member 3a including a layer 2a and a cavity 4a, and a second transducing cell member 3b including a layer 2b and a cavity 4b are preferably contained within the same substrate; and layers 2a and 2b are preferably integrally made. A first pair of electrodes including electrodes 6a and 8a is attached to layer 2, and a second pair of electrode including electrodes 6b and 8b is attached to layer 2b. Electrodes 6a, 8a, 6b and 8b are electrically connected to an electrical circuit by mechanism of conducting lines 37a, 35a, 37b and 35b, respectively, the electrical circuit including a switching element, so as to alternately switch the electrical connections of conducting lines 37a, 35a, 37b and 35b, so as to alternately provide parallel and anti-parallel connections, substantially as described for FIG. 7a, thereby alternately decreasing and increasing the mechanical impedance of layers 2a and 2b.

Figure 7E:
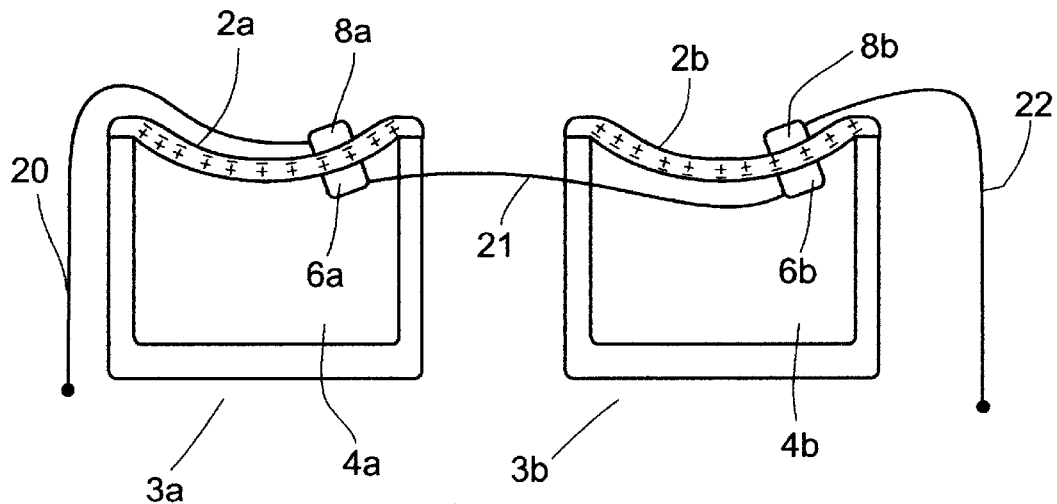

FIG. 7e illustrates another embodiment, wherein the first and second transducing cell members are interconnected by mechanism of an anti-parallel connection. As shown in the Figure, the polarity of layer 2a is opposite to the polarity of layer 2b, so as to reduce the complexity of the electrical connections between cell members 3a and 3b. Thus, electrode 6a is connected to electrode 6b by mechanism of a conducting line 21, and electrodes 8a and 8b are provided with conducting lines 20 and 22, respectively, for connection to an electrical circuit which includes a switching element, wherein the switching element preferably functions as an on/off switch, so as to alternately increase the mechanical impedance of layers 2a and 2b.

Figure 7F:
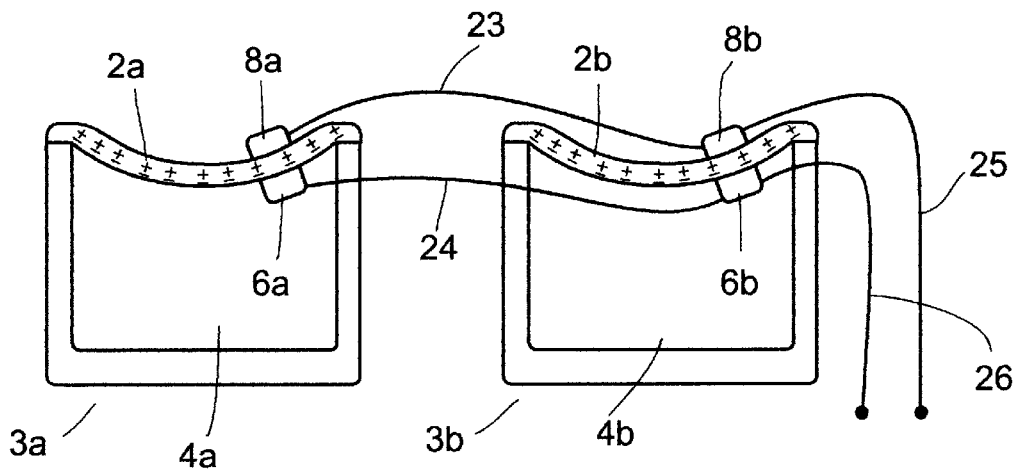

FIG. 7f shows another embodiment, wherein the first and second transducing cell members are interconnected by mechanism of a parallel connection. As shown, electrodes 6a and 6b are interconnected by mechanism of conducting line 24, electrodes 8a and 8b are interconnected by mechanism of conducting line 23, and electrodes 6b and 8b are provided with conducting lines 26 and 25, respectively, the conducting lines for connection to an electrical circuit including a switching element. The switching element preferably functions as an on/off switch for alternately decreasing and increasing the mechanical impedance of layers 2a and 2b.

Figure 8:
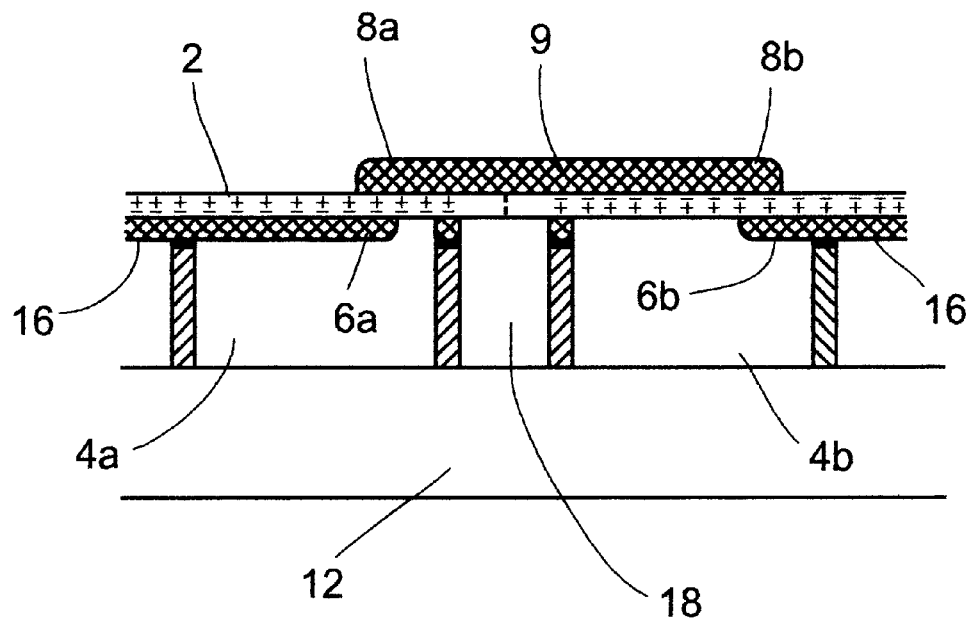
FIG. 8 is a longitudinal section of a transmitter element according to the present invention including an anti-parallel electrical connection.

FIG. 8 shows a possible configuration of two transducing cell members etched onto the same substrate and interconnected by mechanism of an anti-parallel connection. As shown in the Figure, the transducing cell members are covered by a common piezoelectric layer 2, wherein the polarity of the portion of layer 2 received between electrodes 6a and 8a is opposite to the polarity of the portion of layer 2 received between electrodes 6b and 8b. Electrodes 8a and 8b are bonded by mechanism of a conducting line 9, and electrodes 6a and 6b are provided with conducting lines 16 for connection to an electrical circuit.

Figure 9:
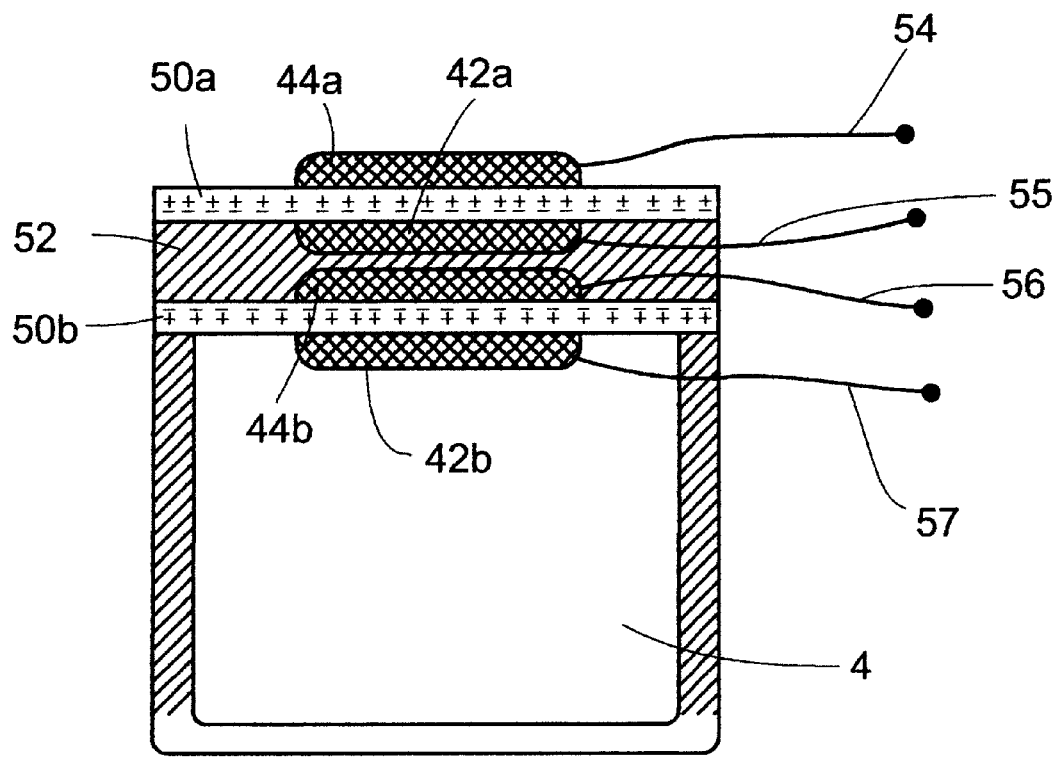
FIG. 9 is a longitudinal section of another embodiment of a transmitter element according to the present invention.

Another embodiment of a transmitter element according to the present invention is shown in FIG. 9. The transmitter element includes a transducing cell member having a cavity 4 covered by a first and second piezoelectric layers, 50a and 50b, preferably having opposite polarities. Preferably, layers 50a and 50b are interconnected by mechanism of an insulating layer 52. Attached to layer 50a are upper and lower electrodes 44a and 42a, and attached to layer 50b are upper and lower electrodes 44b and 42b. Electrodes 44a, 42a, 44b and 42b are provided with conducting lines 54, 55, 56 and 57, respectively, for connection to an electrical circuit.

It will be appreciated that the above descriptions are intended only to serve as examples, and that many other embodiments are possible within the spirit and the scope of invention described in U.S. patent application Ser. No. 09/000,553.

As is detailed hereinunder, in preferred embodiments, the present invention exploits the advantages of the acoustic transducer described hereinabove and in U.S. patent application Ser. No. 09/000,553.

Thus, according to the present invention there is provided an implantable biosensor system, which is referred to hereinunder as biosensor 100.

Biosensor 100 is implantable within a patient's body for monitoring a physiological condition therein. In the course of its operation, biosensor 100 relays, on command, information in the form of acoustic signals pertaining to a parameter or parameters associated with the physiological condition as these are sensed by an implanted sensor or sensors. Furthermore, biosensor 100 according to the present invention is designed to be energized via an external acoustic interrogation signal.

As such, biosensor 100 is wire and/or integral power source independent. In addition, since the human body is, in effect, a water body and further since acoustic radiation is readily propagatable, if so desired, within water bodies in all directions, biosensor 100 of the present invention provides advantages over the prior art in terms of effective implantable depth within the body and further in terms of interrogation signal positional effect.

As further detailed hereinunder, according to a preferred embodiment of the present invention biosensor system 100 incorporates a shunt for alleviating a monitored physiological condition.

Figure 10:
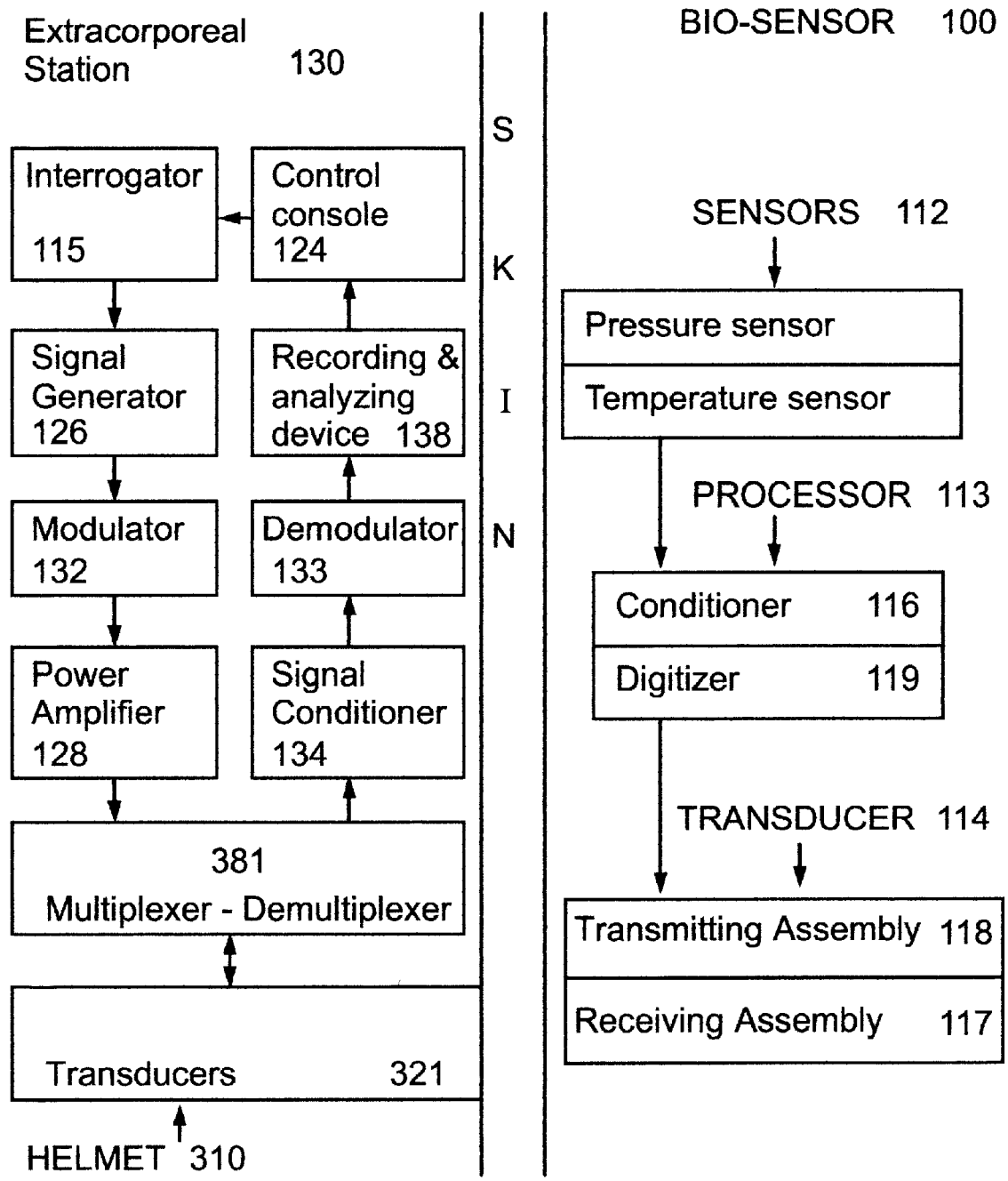
FIG. 10 is a block diagram depicting the intrabody and extracorporeal components of the biosensor system according to the present invention.

As shown in FIG. 10, and according to one embodiment of the present invention, when implanted in a monitoring or treatment intra body site, biosensor 100 of the present invention is employed for sensing or monitoring one or more parameters of a physiological condition within the patient and for transmitting acoustic signals representative of this physiological condition or these parameters out of the patient's body.

According to this embodiment of the present invention, biosensor 100 includes one or more sensors 112 for sensing, monitoring or measuring one or more parameters of the physiological conditions of the patient.

Biosensor 100 also includes an acoustic activatable transducer 114. Transducer 114 serves for receiving electrical signals from sensors 112 and for converting such electrical signals into acoustic signals. Transducer 114 also serves for receiving externally generated acoustic interrogation signals and for converting such acoustic energy into electrical power which is used for energizing sensors 112 and for rendering biosensor 100 wire and integral power source independent.

As further shown in FIG. 10, transducer 114 includes a receiving assembly 117 and a transmitting assembly 118, preferably both are integrated into a single transceiver assembly.

According to a preferred embodiment of the present invention receiving assembly 117 and transmitting assembly 118 are assembled of transducer element 1, the construction of which is further detailed hereinabove with regards to FIGS. 1a, 1b and 2a–2e. Alternatively, a plurality of transducer elements 1 can also be utilized in various configurations (as shown in FIGS. 7b–f, 8 and 9 hereinabove) in the receiving assembly 117 and transmitting assembly 118 of biosensor 100 of the present invention The components of transducer 114 can be formed from separate transducer element 1 units, although the integration of one transducer element 1 into a transceiver is preferred, due to the high degree of miniaturization required in biosensing devices.

According to a preferred embodiment of the present invention signals received and/or transmitted by biosensor 100 are processed by a processor 113. Electrical signals generated by sensors 112 are processed through processor 113 and are forwarded in their processed or converted form to transducer 114. In addition, acoustic signals received by transducer 114 and which are converted to electrical signals (and power) thereby, are preferably further processed by processor 113.

To this end, processor 113, preferably includes a conditioner 116 and, when necessary, a digitizer 119 for processing the electrical signals received thereby from sensors 112 and/or transducer 114.

The acoustic interrogation signal is generated by an extracorporeal station 130 which includes an interrogator 115 and which is also illustrated in FIG. 10, the operation and construction of which is described in further detail below.

Sensors 112 are operable for monitoring or detecting one or more physiological conditions within the patient's body, such as the pressure and/or the temperature of the cerebrospinal fluid in the cavities or ventricles of the patient's brain. Sensors 112 then generate sensor signals representative of these measured physiological parameters. The sensor signals are typically electrical analog signals but may also be digital, depending on the type of sensor employed. It will be appreciated that sensors having a built-in analog-to-digital converter are well known in the art.

Sensors 112 are preferably conventional in construction and may include, for example, pressure sensors, temperature sensors, pH sensors, blood sugar sensors, blood oxygen sensors, or any other type of physiological sensing, monitoring or measuring devices responsive to, for example, motion, flow, velocity, acceleration, force, strain, acoustics, moisture, osmolarity, light, turbidity, radiation, electromagnetic fields, chemicals, ionic, or enzymatic quantities or changes, electrical and/or impedance.

Examples of these and other sensor devices useful in context of the present invention are described in detail in the AIP Handbook of Modern Sensors by Jacob Fraden, hereby incorporated by reference.

In a preferred embodiment, sensors 112 are pressure sensor transducers such as the PVDF sensors described in U.S. patent application Ser. No. 09/161,658, which is incorporated herein by reference, or the MPX2000 series pressure sensors distributed by Motorola.

As mentioned above according to a preferred embodiment of the present invention transducer 114 is electrically coupled to sensors 112 through processor 113. Processor 113 conditions the sensor signals via conditioner 116, converts the sensor signals to a digital form (when so required) via digitizer 119, and provides the processed or converted signal to transducer 114. Upon a command, transducer 114 converts the processed electrical signals into corresponding acoustic signals which are concomitantly transmitted out of the patient's body, when subjected to an acoustic interrogation signal from station 130.

In more detail, processor 113 is electrically connected to sensors 112 and both share a common miniature substrate such as is customary in the VLSI (Very Large Scale Integration) industry. Processor 113 directly receives sensors' 112 signals by, e.g., the shortest possible wiring.

Processor 113 serves several functions. As already mentioned, processor 113 conditions via conditioner 116 the signals received from sensors 112. Such conditioning is necessary due to the miniature size and small capacitance of sensors 112, and as such, conditioner 116 provides not only appropriate amplification and filtering, but also impedance reduction, so as to substantially reduce noise pickup and thereby improve the signal-to-noise ratio of biosensor 100.

In addition, digitizer 119 is employed in processor 113 to convert the analog signals to digital signals and format the digitized signals as a binary data stream for transmission out of the patient by transducer 114 acoustic signals, which are received and interpreted by extracorporeal station 130.

Processor 113 is also operable for coding and formatting a unique device identification number for transmission with the sensors' signals for use in identifying a specific transducer 114 and/or sensor 112.

Preferably, processor 113 can be programmed to analyze the monitored signals before transmitting the signals out of the patient's body. To this end, processor 113 can be provided with a memory device and a programmable microprocessor. Many more tasks which are applicable to biosensor system 100 of the present invention can be provided by processor 113, such as, for example, calculating a reading by correlating information derived from a plurality of sensors 112.

For example, if biosensor 100 is provided with a pressure sensor and a temperature sensor for measuring both the pressure and temperature of the cerebrospinal fluid in the patient's brain, processor 113 can then be programmed to adjust the pressure signal transmitted out of the patient's body to compensate for higher or lower temperature readings as sensed by the temperature sensor and vice versa, thereby providing more accurate readings.

It will, however, be appreciated by one ordinarily skilled in the art that sole or additional/supplementary processing can be effected by processors present in extracorporeal station 130.

Preferably, transmitting assembly 118 of transducer 114 employs modulations or other methods in modifying the transmitted acoustic signal, such modulation methods are well known in the art and are described in detail in, for example, U.S. Pat. No. 5,619,997 which is incorporated herein by reference.

Extracorporeal station 130 is located outside the patient's body and is designed for powering or energizing transducer 114 of biosensor 100 which is implanted within the patient's body, and for receiving the sensors' acoustic signals.

Figure 11:
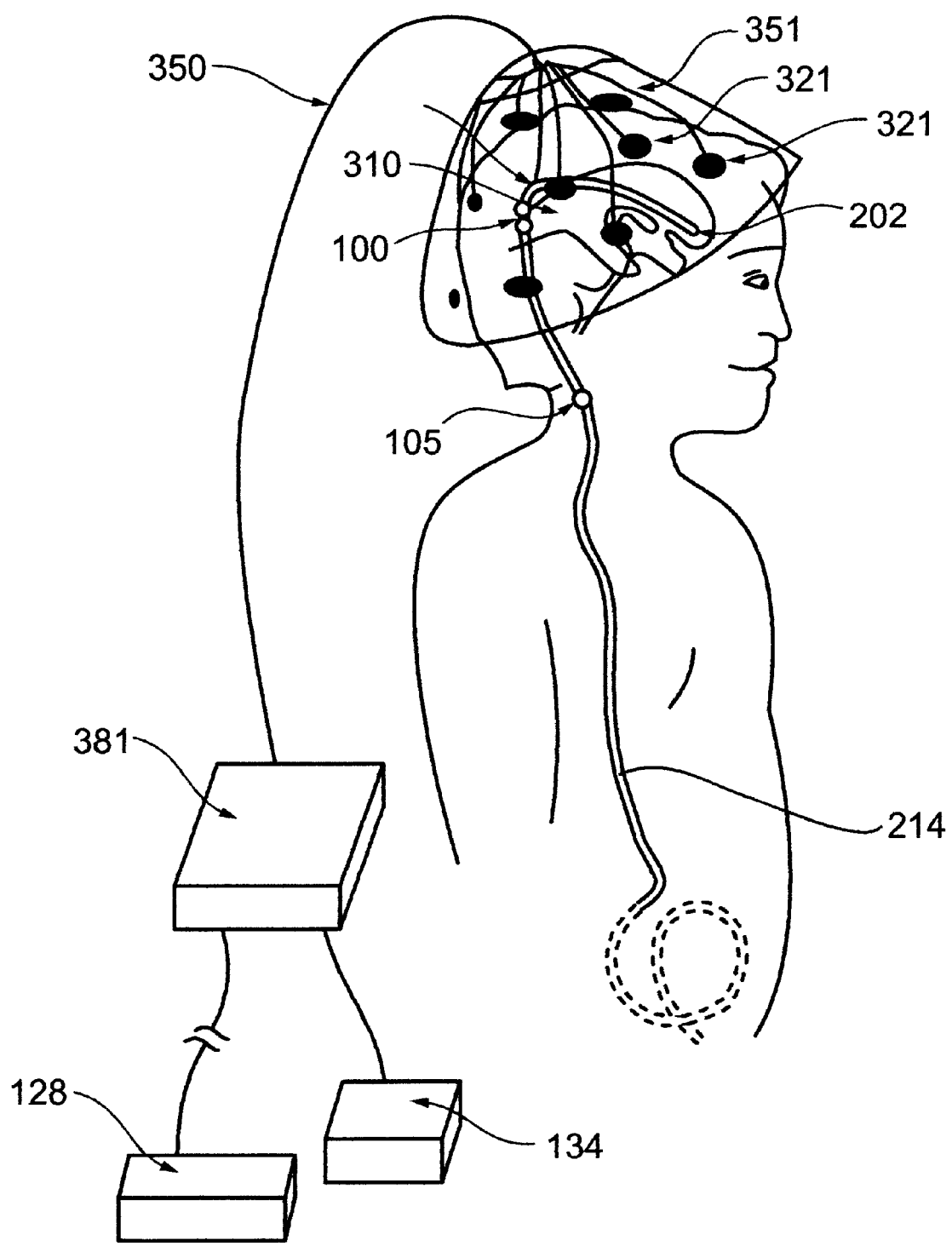
FIG. 11 is a schematic depiction of components of the biosensor system according to one embodiment of the present invention.

As illustrated in FIGS. 10–11, according to one embodiment of the present invention and as further detailed in the following sections, transducers 321 of station 130 are mounted within a helmet 310. Transducers 321 are coupled via wiring with a signal generator 126, a power amplifier 128, a modulator 132, a demodulator 133, a signal conditioner 134 and a recording and analyzing device 138.

Signal generator 126 and power amplifier 128 provide energy to extracorporeal transducer 321 for generating acoustic signals which propagate from the surface into the patient's body and energize intrabody acoustic transducer 114 when impinging thereon. Signal generator 126 and power amplifier 128 may be of any known type, including devices constructed in accordance with "Data Transmission from an Implantable Biotelemeter by Load-Shift Keying Using Circuit Configuration Modulator" by Zhengnian Tang, Brian Smith, John H. Schild, and P. Hunter Peckham, IEEE Transactions on Biomedical Engineering, vol. 42, No. 5, May, 1995, pp. 524–528, which is incorporated herein by reference.

As already mentioned, transducers 321 are preferably of a type functionally similar to transducer element 1, the construction of which is further described hereinabove in FIGS. 1a, 1b, 2a–2e, 7b–f, 8 and 9, each of which can serve as a transmitter, receiver or a transceiver, and are preferably constructed to comply with NCRP 113: Exposure criteria for medical diagnostic ultrasound 1992, parts I and II, provided that transducers 321 when serve as a powering transmitter is capable of transmitting sufficient energy in the form of an acoustic signal for energizing biosensor 100. Preferred transducers 321 include commercial piston type transducers.

Transducers 321 are electrically connected to power amplifier 128 and acoustically communicable with transducer 114. Transducers 321 transform and deliver the energy generated by generator 126 and power amplifier 128 to transducer 114 via the body of the patient, which serves in this respect as a water body.

Demodulator 133 is operatively coupled to transducers 321 and is provided for extracting digital data received thereby from transducer 114. An example of a demodulator 133 that can be used in interrogator 115 of extracorporeal station 130 is the MC1496 or MC1596 type demodulator distributed by Motorola.

Signal conditioner 134 is connected to demodulator 133 for converting the demodulated data to a format suitable for recording or storing in external devices. An example of a signal conditioner 134 that can be used in station 130 of the present invention is the ADM202 type conditioner distributed by Analog Devices. Signal conditioner 134 may be connected with conventional recording and/or analyzing devices such as computers, printers, and displays for recording, presenting and/or further analyzing the signals transmitted by biosensor 100.

Thus, and according to this embodiment of the present invention, biosensor 100 described hereinabove is implanted in a patient for sensing, monitoring or detecting one or more parameters associated with a physiological condition of the patient. When it is desired to collect information from the body of the patient, a control console 124 commands interrogator 115 to trigger an energizing signal output from signal generator 126. The energizing signal is then modulated with other commands originating from control console 124 that governs processor 113 of biosensor 100 and multiplexer-demultiplexer 381. The modulated signal is amplified by power amplifier 128 and sent to transducer 321 to energize and render biosensor 100 operative via transducer 114 thereof The energy thus provided through the body of the patient is also used to provide transducer 114 with energy to produce an acoustic signal related to the information thus collected by sensors 112. To this end, transducers 321 of station 130 are placed in intimate physical contact with a portion of the patient's body preferably in which biosensor 100 is implanted. Station 130 generates an acoustic interrogation signal via transducers 321 for powering biosensor 100 and for retrieving via transducers 114 sensors' 112 signals as an acoustic signal generated by transducer 114. Interrogator 115 then demodulates sensors' 112 signals and delivers the signals to recording and analyzing device 138.

It will be appreciated that in cases where each of sensors 112 provides information pertaining to a specific parameter, specific information from each of sensors 112 can be accessed by station 130 by providing a unique identifying code for each sensor with the acoustic interrogation signal. Such a code would be interpreted by processor 113 to command the retrieval of information from any specific sensor of sensors 112.

Figure 12:
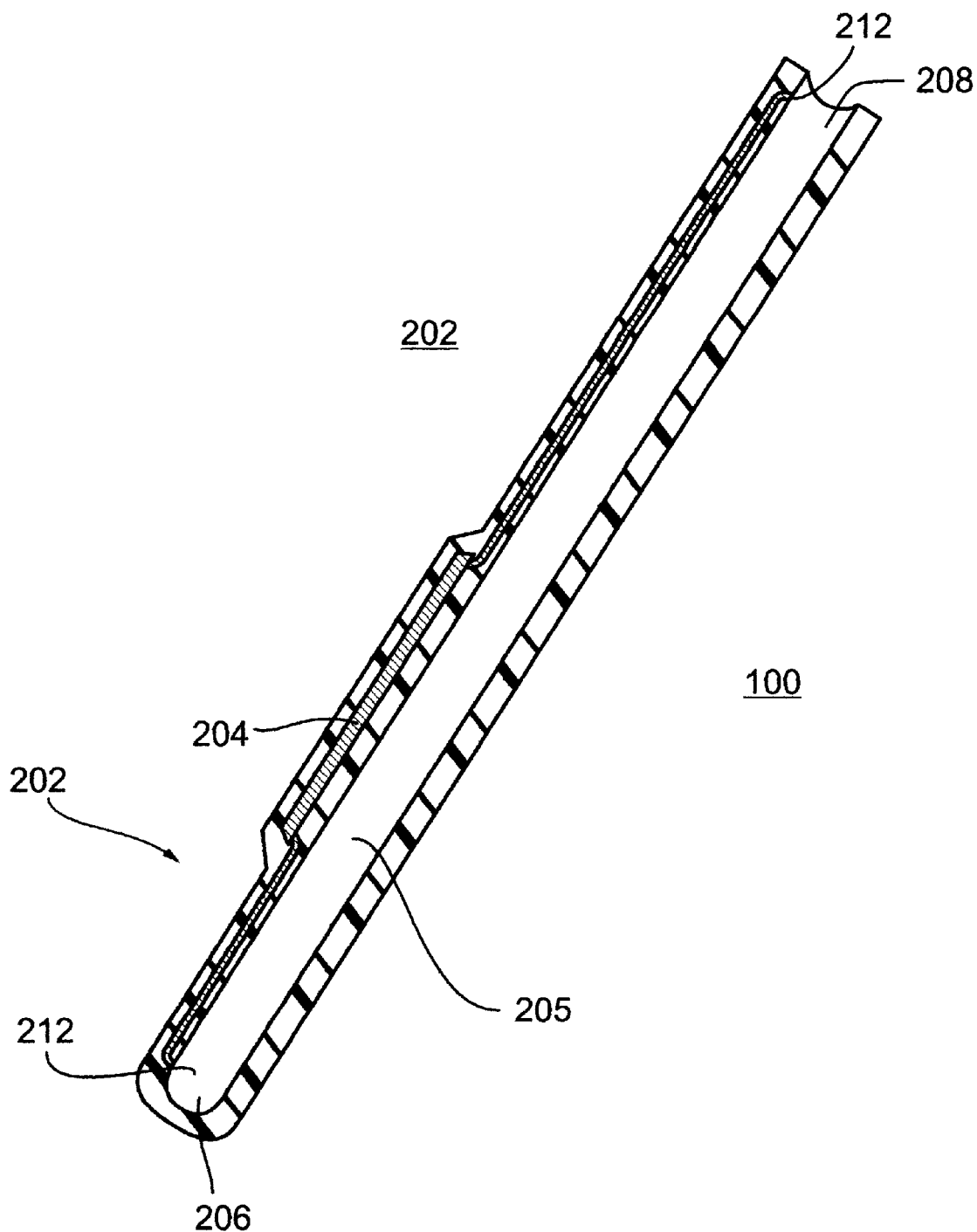
FIG. 12 is a longitudinal section of a shunt system including an acoustic transducer and pressure sensors according to another embodiment of the present invention.
Figure 13:
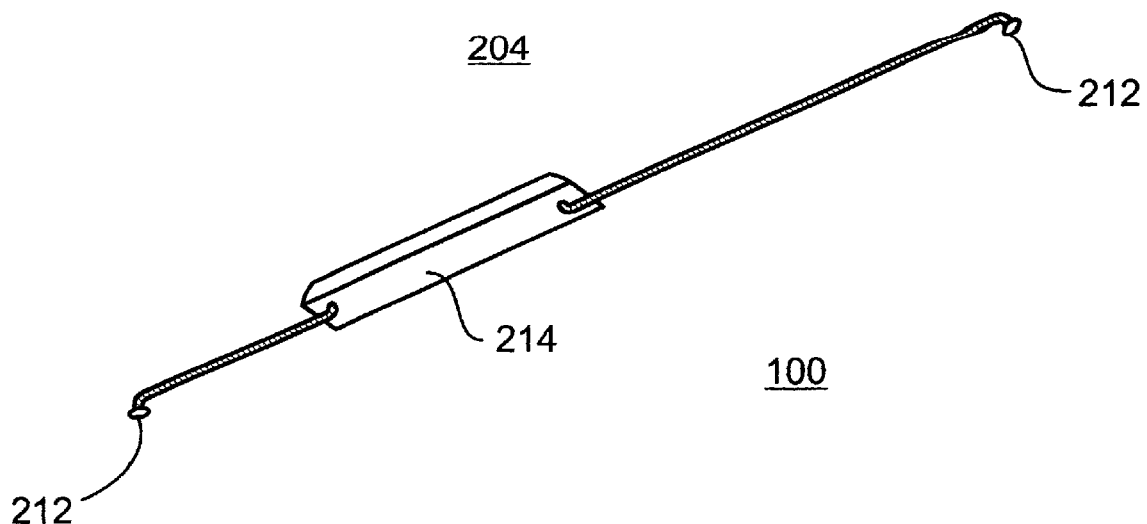
FIG. 13 is a schematic depiction of the transducer and pressure sensors of FIG. 12 isolated from the shunt.

Referring now to FIGS. 11–13. According to another preferred embodiment of the present invention and as best illustrated in FIG. 12, biosensor 100 further includes a shunt 202 for draining fluid from a portion of a patient's body, and a monitoring device 204 which is further detailed hereinbelow with respect to FIG. 13. According to a preferred embodiment, monitoring device 204 is embedded within the walls of shunt 202 for non-invasively monitoring the operation of shunt 202.

In more detail, shunt 202 according to this embodiment of the present invention is a cerebrospinal fluid shunt and is used for draining cerebrospinal fluid from a patient's brain, when so required. Cerebrospinal fluid shunt 202 is preferably formed of medical grade synthetic resin material and presents opposed ventricular 206 and distal 208 ends connected by a fluid passageway 205 which includes a valve 105. When shunt 202 is implanted in a patient, ventricular end 206 is positioned in a ventricular cavity of the patient's brain and distal end 208 is positioned in an organ or body cavity remote from the ventricular cavity so as to drain fluids from the patient's brain thereto.

As shown in FIG. 11, an appropriate site to drain the cerebrospinal fluid out of the brain may be the abdomen cavity. A further appropriate site for drainage is immediately after valve 105, in order to make the shunt tubing as short as possible and largely simplify the implantation thereof in surgery. Such drainage is effected via a tube 214 leading from shunt 202 to the patients abdominal cavity. Another appropriate site for draining cerebrospinal fluid out of the patient's brain may be the patient's skull, close to the spine. In this case the drainage tube is much shorter, simplifying the implantation surgery and reducing the risk to the patient. In both case, valve 105 which forms a part of, and is operable by, biosensor 100 is preferably used for alleviating intracranial pressure via shunt 202.

As best illustrated in FIG. 12, monitoring device 204 is preferably formed or embedded within the sidewall of shunt 202.

Referring to FIG. 13, monitoring device 204 preferably includes one or more pressure sensors 212 and a transducer 214 which is electrically coupled with sensors 212. Like sensors 112, sensors 212 can include, for example, temperature sensors, pH sensors, blood sugar sensors, blood oxygen sensors, or any other type of physiological sensing, monitoring or measuring device responsive to, for example, motion, flow, velocity, acceleration, force, strain, acoustics, moisture, osmolarity, light, turbidity, radiation, electricity, electromagnetic fields, chemicals, ionic, or enzymatic quantities or changes.

According to a preferred embodiment of the present invention, sensors 212 are provided for sensing the pressure of the cerebrospinal fluid in shunt passageway 205 and are preferably spaced a distance apart from one another for sensing pressure at different points within passageway 205. Sensors 212 may be placed anywhere within shunt 202 and may include piezoelectric or piezo-resistive transducers, silicon capacitive pressure transducers, variable-resistance laminates of conductive ink, variable conductance elastomeric devices, strain gauges or similar types of pressure sensitive devices.

Transducer 214 is also preferably formed or embedded within the sidewall of the shunt 202 and is coupled with sensors 212 for directly or indirectly (via a processor) receiving electrical pressure signals therefrom.

According to this embodiment of the present invention biosensor 100 which includes monitoring device 204 is implanted in a patient as illustrated generally in FIG. 11 for draining or removing cerebrospinal fluid from the patient's brain for treating hydrocephalus. Monitoring device 204 which is preferably formed within the sidewalls of shunt 202 senses or detects the pressure of the cerebrospinal fluid within shunt 202 and delivers pressure signals to transducer 214. Preferably such monitoring is performed by sensors 212 periodically. Such periodic readings can be stored and processed within a processor for later access.

When it is desired to collect information from sensors 212, station 130 (or at least transducers 321 thereof) is placed adjacent a portion of the patient's body in which biosensor 100 is implanted. As described before, station 130 generates an interrogation signal delivered through transducers 321 for concomitantly powering biosensor 100 and retrieving data therefrom via transducer 214 in a fashion similar to as described above with respect to transducer 114. Should the data collected indicate an abnormal intracranial pressure, valve 105 of shunt 202 is opened to drain cerebrospinal fluid therethrough. To this end station 130 can be commanded to provide power for the opening of valve 105. This operation can be controlled either manually or by a preprogrammed processor.

Figure 14:
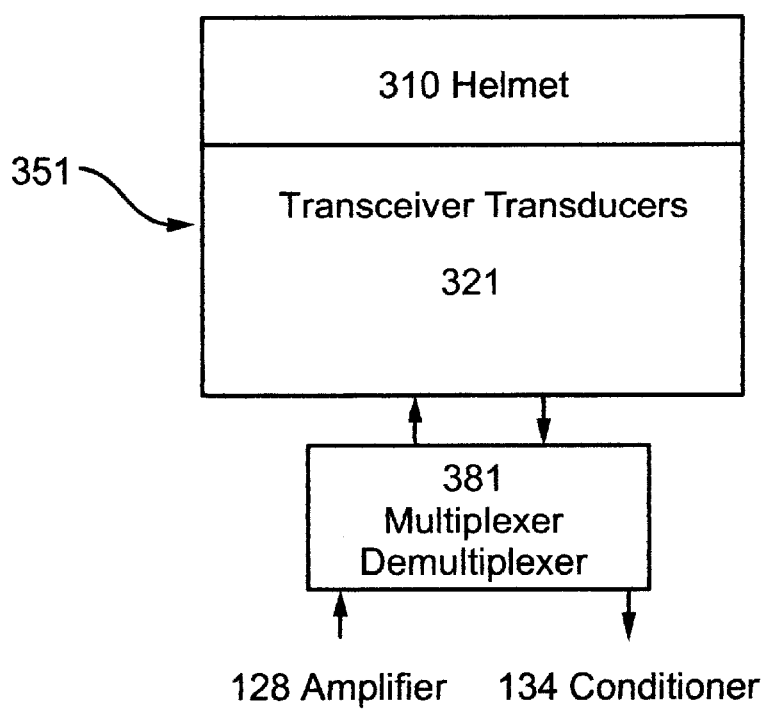
FIG. 14 is a block diagram of the extracorporeal station components according to the present invention implemented within a helmet.

According to another preferred embodiment of the present invention and as shown in FIGS. 11 and 14 there is provided a transducing assembly 351 which forms a part of station 130. In one configuration, as best seen in FIG. 11, assembly 351 is incorporated into a helmet 310. Helmet 310 includes a plurality of transducers 321, each may serve as a transmitter, receiver or transceiver, positioned at various locations so as to provide full transmittance/reception spatial coverage of the brain volume.

As shown in FIG. 11, a cable bundle 350 physically connects assembly 351 to multiplexer/demultiplexer 381, which is computer controlled. Multiplexer/demultiplexer 381 serves several functions, including (i) providing a transmittance signal to transducers 321 from power amplifier 128; (ii) conveying sensors' 112 or 212 signals from the body to signal conditioner 134; (iii) providing a computer-controlled multiplexing for transducers 321 when used as transmitters; (iv) providing multiplexing for transducers 321 when used as receivers; and/or (v) providing decoupling between the high power transmission signals from amplifier 128 and the low amplitude signals received from transmitting assembly 118 which is located within the body, into signal conditioner 134. It will be appreciated that multiplexer/demultiplexer 381 both isolates and routes the transmitted and received signals.

According to a preferred embodiment of the present invention the operation of assembly 351 included within helmet 310 is effected following pre calibration of the required location of the transducers over the helmet by, preferably, applying a method which is based on a positioning model.

Such a positioning model allows for an accurate placement of the extracorporeal transducers such that acoustic insonifying of the brain volume is provided at an approximately uniform level throughout.

In addition, to achieve such uniformity a three dimensional acoustic propagation model of the skull and brain can also be applied.

Employment of wide beam low frequency ultrasonic transducers may be advantageous in providing an economical coverage.

In addition, focusing the acoustic beams of the extracorporeal transducers on the intrabody transducer is also advantageous because in such cases narrow beam transducers of low frequency ultrasound can be efficiently utilized.

Thus, for appropriately positioning such extracorporeal transducers, either a positioning model or a converging (in-fire) spheroidal acoustic array model with scattering can be used to provide the positional information required. With each of the transducers configuration envisaged above, a first run calibration session is employed in which communication between the helmet (extracorporeal) transducers and the intrabody transducer is tested for maximal accuracy.

The present invention is advantageous over the existing art because it employs acoustic signals which are more readily propagatable in water bodies, such as the human body, as compared to radio frequency signals.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. An implantable biosensor system for monitoring a physiological condition in a patient, the biosensor system comprising:

(a) at least one sensor for sensing at least one parameter of a physiological condition and for generating an electrical sensor signal representative of the physiological condition; and (b) at least one first acoustic activatable transducer being directly or indirectly coupled with said at least one sensor, said at least one first acoustic activatable transducer being for converting a received acoustic interrogation signal from outside the patient's body into an electrical power for energizing said at least one sensor, said at least one first acoustic activatable transducer further being for converting said electrical sensor signal of said at least one sensor into an acoustic signal receivable out of the patient's body, such that information pertaining to said at least one parameter of the physiological condition can be relayed outside the patient's body upon generation of an acoustic interrogation signal.

2. The biosensor system of claim 1, wherein said at least one first acoustic activatable transducer includes:

(i) a cell member having a cavity;

(ii) a substantially flexible piezoelectric layer attached to said cell member, said piezoelectric layer having an external surface and an internal surface, said piezoelectric layer featuring such dimensions so as to enable fluctuations thereof at its resonance frequency upon impinging of said acoustic interrogation signal; and (iii) a first electrode attached to said external surface and a second electrode attached to said internal surface.

3. The biosensor system of claim 2, wherein said piezoelectric layer is of a material selected from the group consisting of PVDF and piezoceramic.

* * * * *